US011081217B2

(12) United States Patent
Zarkoob et al.

(10) Patent No.: US 11,081,217 B2
(45) Date of Patent: Aug. 3, 2021

(54) SYSTEMS AND METHODS FOR OPTIMAL HEALTH ASSESSMENT AND OPTIMAL PREVENTIVE PROGRAM DEVELOPMENT IN POPULATION HEALTH MANAGEMENT

(71) Applicant: BaseHealth, Inc., Sunnyvale, CA (US)

(72) Inventors: Hadi Zarkoob, Sunnyvale, CA (US); Emin Martinian, Wellesley, MA (US); Prakash Menon, Cupertino, CA (US); Jason Pyle, Campbell, CA (US); Hossein Fakhrai-Rad, Los Altos, CA (US)

(73) Assignee: BASEHEALTH, INC., Sunnyvale, CA (US)

( * ) Notice: Subject to any disclaimer, the term of this patent is extended or adjusted under 35 U.S.C. 154(b) by 250 days.

(21) Appl. No.: 16/230,487

(22) Filed: Dec. 21, 2018

(65) Prior Publication Data
US 2019/0198140 A1 Jun. 27, 2019

Related U.S. Application Data

(60) Provisional application No. 62/608,902, filed on Dec. 21, 2017.

(51) Int. Cl.
G16H 10/60 (2018.01)
G16H 50/20 (2018.01)
G16H 50/30 (2018.01)
G16H 50/70 (2018.01)
G16H 20/00 (2018.01)
G16H 40/20 (2018.01)

(52) U.S. Cl.
CPC ............. *G16H 10/60* (2018.01); *G16H 20/00* (2018.01); *G16H 50/20* (2018.01); *G16H 50/30* (2018.01); *G16H 50/70* (2018.01); *G16H 40/20* (2018.01)

(58) Field of Classification Search
CPC ...................................... G16H 10/60
See application file for complete search history.

(56) References Cited

U.S. PATENT DOCUMENTS

2008/0147441 A1* 6/2008 Kil .......................... G06F 19/00
705/2
2010/0070455 A1* 3/2010 Halperin ............... G16B 20/00
706/54

(Continued)

OTHER PUBLICATIONS

Wiley, https://onlinelibrary.wiley.com/doi/pdf/10.1111/jep.12752 (Year: 2017).*

*Primary Examiner* — Michael Tomaszewski
*Assistant Examiner* — Jay M. Patel
(74) *Attorney, Agent, or Firm* — Dickinson Wright PLLC

(57) ABSTRACT

Various health management systems may benefit from tools for appropriate identification of target patients. For example, various population health management approaches may benefit from systems and methods for optimal health assessment and optimal preventative program development. A method can include obtaining a simple risk measure score for a patient. The method can also include obtaining an evidence-based score for the patient. The method can further include comparing the simple risk measure score to the evidence-based score. The method can additionally include identifying the patient as a target for preventative medicine based on a discrepancy revealed by the comparison.

3 Claims, 2 Drawing Sheets

(56) References Cited

U.S. PATENT DOCUMENTS

| | | | |
|---|---|---|---|
| 2011/0178815 A1* | 7/2011 | Levett | G16H 50/70 705/2 |
| 2011/0294681 A1* | 12/2011 | Hinds | A61P 35/00 506/9 |
| 2013/0204644 A1* | 8/2013 | Evans | G06Q 10/10 705/4 |
| 2014/0006039 A1* | 1/2014 | Khan | G06Q 10/0639 705/2 |
| 2014/0088442 A1* | 3/2014 | Soykan | A61B 5/6866 600/483 |
| 2014/0365276 A1* | 12/2014 | Harsha | G06Q 30/0202 705/7.31 |
| 2015/0019255 A1* | 1/2015 | Coetzer | G06Q 10/0639 705/3 |
| 2016/0374608 A1* | 12/2016 | Dugan | A61B 5/1114 600/301 |
| 2017/0037475 A1* | 2/2017 | Ho | C12Q 1/6883 |
| 2017/0242021 A1* | 8/2017 | Chaiworapongsa | A61K 31/616 |
| 2017/0242972 A1* | 8/2017 | Hu | G16H 50/70 |
| 2017/0300911 A1* | 10/2017 | Alnajem | G06Q 10/0635 |
| 2018/0020021 A1* | 1/2018 | Gilmore | H04L 63/1441 |
| 2018/0082317 A1* | 3/2018 | Reier | G06Q 10/10 |
| 2018/0211727 A1* | 7/2018 | Zarkoob | G16C 20/70 |
| 2018/0270266 A1* | 9/2018 | Zoldi | G06Q 10/0635 |
| 2018/0350451 A1* | 12/2018 | Ohnemus | G16H 20/30 |
| 2018/0374581 A1* | 12/2018 | Berringer | G16H 50/30 |

\* cited by examiner

SYSTEMS AND METHODS FOR OPTIMAL HEALTH ASSESSMENT AND OPTIMAL PREVENTIVE PROGRAM DEVELOPMENT IN POPULATION HEALTH MANAGEMENT

CROSS-REFERENCE TO RELATED APPLICATION

This application is a non-provisional of, and claims the benefit and priority of, U.S. Provisional Patent Application No. 62/608,902, filed Dec. 21, 2017, the entirety of which is hereby incorporated herein by reference.

BACKGROUND

Field

Various health management systems may benefit from tools for appropriate identification of target patients. For example, various population health management approaches may benefit from systems and methods for optimal health assessment and optimal preventative program development.

Related Art

Modern health care systems serve a wide range of patients with different conditions. Electronic health records (EHRs) and decision support tools can assist that effort.

Patients often do not know what specific risk factor(s) they carry for a health condition and they do not know what intervention they need or how to obtain it. By using EHRs to review patient data before serious health problems occur, health care systems can lower costs and keep patients healthier.

In one approach, a team of highly trained specialists would review each patient's health record and devise a personalized plan to help the patient attain optimal health. Such a review would account for the patient's individual genetic blue print, age, vital signs, past history, or the like in a scientific and evidence-based way.

SUMMARY

According to certain embodiments, a method can include obtaining a simple risk measure score for a patient. The method can also include obtaining an evidence-based score for the patient. The method can further include comparing the simple risk measure score to the evidence-based score. The method can additionally include identifying the patient as a target for preventative medicine based on a discrepancy revealed by the comparison.

In certain embodiments, an apparatus can include at least one processor and at least one memory including computer program instructions. The at least one memory and the computer program instructions can be configured to, with the at least one processor, cause the apparatus at least to perform a process. The process can include obtaining a simple risk measure score for a patient. The process can also include obtaining an evidence-based score for the patient. The process can further include comparing the simple risk measure score to the evidence-based score. The process can additionally include identifying the patient as a target for preventative medicine based on a discrepancy revealed by the comparison.

A non-transitory computer-readable medium can, according to certain embodiments, be encoded with instructions that, when executed in hardware, perform a process. The process can include obtaining a simple risk measure score for a patient. The process can also include obtaining an evidence-based score for the patient. The process can further include comparing the simple risk measure score to the evidence-based score. The process can additionally include identifying the patient as a target for preventative medicine based on a discrepancy revealed by the comparison.

BRIEF DESCRIPTION OF THE DRAWINGS

The accompanying drawings are provided for purposes of illustration and not by way of limitation.

DETAILED DESCRIPTION

Figure 1:
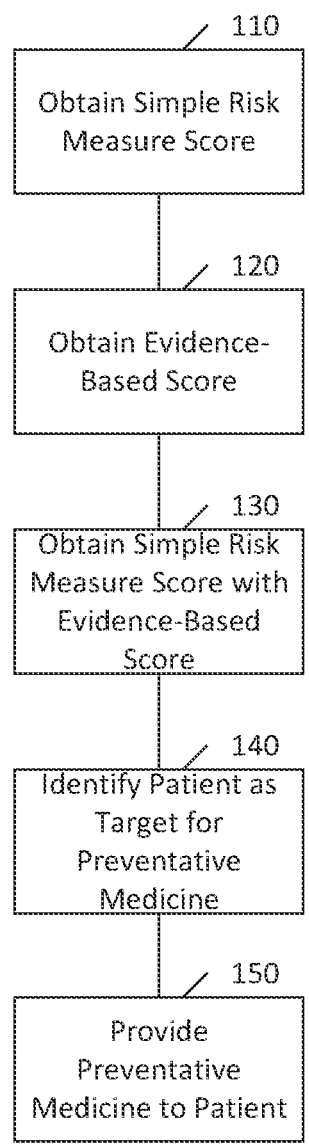
FIG. 1 illustrates a method according to certain embodiments.

Certain embodiments relate to applying machine learning and artificial intelligence decision support tools to engage with patient's health data and find opportunities for health improvement and preventive care.

More particularly, certain embodiments relate to a system for intelligently connecting with patients, using decision support and machine learning tools that find a cost effective engagement plan for each patient individually. The system may work by ingesting large amounts of patient data (for example, through electronic health records), analyzing the patient's data, and producing a list of patients with high probability of developing health condition(s) who are mostly likely to benefit from further supervision by the health care professionals along with suggestions on interventions for those patients.

A primary goal of certain embodiments is to cost effectively find patients whom the health care system can help pro-actively by reducing their risk of developing a disease, managing their existing health condition, or avoiding complications of the disease. For example, certain embodiments may identify patients whom the health care system can help before they are immediately suffering an acute health problem. This help can involve a visit to the doctor or nurse practitioner, health advice, drug prescriptions, procedures, or other health interventions (for example, an exercise program, nutrition counseling, smoking cessation programs, or the like).

Certain embodiments of a system may work via automated health decision processes which may identify patients who are likely to benefit from preventive care. Furthermore, the system can specify some specific risk factors to investigate for an individual patient. Candidate patients may then be passed along to the next decision process stage which may involve a team of human health navigators that can review the initial list of candidate patients. These patients can then be passed to a team of nurse practitioners who may winnow the list further for the next term of action(s). Then the list can be filtered by a team of human general practitioners, who in turn can refer to specialists and so on if needed.

By using an automated decision process to develop a computer-based list and then winnowing further with human or computer filtering in multiple stages, certain embodiments can very efficiently and accurately screen a vast patient population to find valuable preventive health care interventions.

General Method

Since there are a number of possible variations on how to identify the optimal set of patients, the following describes a general method for patient selection. Later, this general method is specialized with further details.

One insight of the system is that the health care system is already trying to find opportunities to help high risk patients who would benefit the most from high quality preventive care. As a result, producing a list of the sickest patients within the population is unlikely to be helpful. Instead, automated decision tools are more likely to be useful if they can find the patients whom for one reason or another the health care system tends to miss.

A simple risk measure (SRM) can be used by the health care system in question to explicitly or implicitly rank patients. This SRM may involve the following:

1. The total allowed claims data for the patient in the previous period (for example, the previous quarter or year).
2. A risk score such as the CMS HCC risk adjustment model, also referred to as the risk adjustment factor (RAF). For example, see the "HHS-Operated Risk Adjustment Methodology Meeting" whitepaper from Mar. 31, 2016, available on the Center for Medicare Services web site, the contents of which are hereby incorporated by reference.
3. Other types of proprietary risk measures.

Next, using various approaches, the system can provide an evidence-based health assessment of how likely the patient is to suffer health issues and how preventable or manageable such issues may be. This assessment can be referred to as the evidence-based score (EBS).

In many existing health care systems, the SRM is relatively simple. For example, it may exclude things like patient vital signs, blood pressure, pharmaceutical history, demographic information, and a myriad other risk factors which the scientific literature has repeatedly shown are predictive and causative. This is mainly because SRMs were often developed many years ago when either electronic health records did not contain enough information for more sophisticated risk analysis or because more advanced machine learning techniques were not available or for some other reasons which are no longer relevant.

The result is that patients with low SRMs are often considered "healthy" by their health care system and receive less attention than they should, or in some cases no attention at all. They may be at risk of serious health conditions or have significant opportunities to improve their health. Because of a low reported SRM and no acute problems, they are considered to be in a low risk or no risk group of patients who won't be considered to receive needed health support by health care providers.

As a simple example, consider a 70-year old male who is overweight, smokes, and has high blood pressure. These are all significant and manageable risk factors for heart disease, diabetes, stroke, and other serious health problems. Now imagine that for whatever reason (for example, a dislike of needles), this patient has not been to the doctor in the past year. Many SRMs will classify the patient as low risk because such SRMs often only look at the trailing 12 months of patient claims data history reported by healthcare professionals.

Again, in the interest of concreteness, consider the mostly widely used risk measure: the CMS HCC RAF score. A patient like this who has not seen the doctor in the past year will have little or no claims data and will often be characterized as having average risk. This point is worth repeating: a patient with significant and manageable risk factors will be classified as average if not low risk according to the most widely used risk system in the United States and hence generally ignored until an acute health issue arises. At that point, the health outcome will be much more severe and the health care resources required to treat the patient will be much bigger.

In the system according to certain embodiments, an evidence-based score (EBS) can be used to more intelligently evaluate the patient's overall health status by taking into account more available data. The system may then compare the EBS to the SRM in various ways and identify patients that the health care system is essentially designed to ignore who could get most benefit from the available intervention opportunities.

For example, one of the methods the system may use is to create a list of patients where the EBS indicates there is significant risk while the SRM indicates low risk. Another method certain embodiments may use is to create a list of patients where the EBS indicates they carry high modifiable risk factors which are not being addressed or managed. These lists may then be provided to teams of health care providers who can address those risk factors.

The health care providers can then triage the patients from the list, engage with them, and bring in promising candidates for further health visits to address the issues raised. This process may generally result in a number of benefits which may include:

1. Patients that the health care system using traditional SRM would generally miss are brought in for further analysis due to an evidence-based procedure. Regardless of the outcome, such patients generally end up with a better relationship with their health care providers as they learn that the system has a full comprehensive view over their health and values their wellbeing. This more favorable and personalized patient experience is valuable.
2. Sometimes significant health problems are identified, and by addressing the corresponding modifiable risk factors to the health problem the health of patient is improved. Even when no risk factors are modified, patients and their health care providers may learn who is at higher risk and can monitor such patients more thoroughly. For example, a patient who is at risk of a heart attack or stroke who for whatever reason does not exercise to reduce the risk, could still learn the signs of a heart attack or stroke so he or she can quickly seek help when such an event occurs.
3. To the extent that health care providers are compensated based on erroneous SRMs, further health visits often end up improving the accuracy of the risk assessment and result in fairer evaluations of value-based contracts.
4. Some health care providers are partially compensated on how well they engage with patients (for example, Medicare Star Ratings). The engagement plan described herein is one efficient way to improve a health care systems ratings by optimally finding patients to connect with.

Risk Factor Quantile Method

The following is a specialization of the general method based on risk quantiles estimated using various machine learning algorithms.

For the purpose of illustration, imagine that the simple risk measure (SRM) is the CMS HCC risk adjustment factor (RAF). To construct the evidence-based score (EBS) the following can be done:

1. Choose an EBS quantile level Q (for example, 80th percentile) and SRM quantile level M (for example, 10th percentile).
2. Collect a patient dataset of N patients.
3. Choose R risk factors that may affect health.
   Examples may include patient age, systolic and diastolic blood pressure, lipid profile such as HDL, LDL, VLDL cholesterol measurements, triglycerides, and hemoglobin A1C and C reactive protein, and body mass index.
4. For patient p and time period t, create the risk factor vector $R_{p,t}$ such that $R_{p,t}^i$ is the reading for the i-th risk factor for patient p in time period t.
   For example, the time period could be the year or quarter such as "2015" or "Fall 2015".
5. For time period t+1, collect the target metric (i.e., the quantity the machine learning system is to predict).
   A common target metric may be the total allowed claims data in period t+1. Other target metrics are possible such as the RAF score in period t+1 or the number of hospital visits in period t+1.
6. Label each patient according to whether the target metric in period t+1 is above or below the chosen quantile level Q. The label for patient p is denoted $L_p$.
   For example, if the system is using Q=80, label patients with the target metric equal to or greater than the 80th percentile with the label "1" and others with the label "0".
7. Train a machine learning algorithm such as a linear regression, logistic regression, random forest, support vector machines, neural networks, or the like, to predict the label for patient p, as a function of the risk factor vector. This can be denoted as $L_p=f(R_{p,t})$ where $f(\cdot)$ represents the machine learning algorithm that is being trained. For patient p, $f(R_{p,t})$ represents the evidence-based score.

Once the machine learning algorithm, $f(\cdot)$, is trained, the system can then use it as follows for time period t':
1. Create a list of patients who have the simple risk measure (SRM) below quantile M in time period t'. (For example, if the system has been trained with data from the years t=2015 and t+1=2016, it can be used for year t'=2017). These may be the patients which the health care system implicitly believes are low risk.
2. Of these patients, select any which are predicted to have high risk according to the evidence-based score. In an example case, this may correspond to the patients with $f(R_{p,t})=1$. These are the "invisible patients": those whom the evidence-based score indicates are high risk but that the health care system is missing.
3. Pass this list of invisible patients to a team of health care professionals to triage and assess.

Risk Factor Trained-Quantile Method

Next, the previously described "Risk Factor Quantile Method" (RFQM) can be understood in a variation referred to as the Risk Factor Trained-Quantile Method (RFTQM). RFTQM is like the previously discussed RTQM except for the data used in the training step.

In RFTQM, the machine learning algorithms can be trained based only on the data points at which the SRM is below the quantile M. The zero/one labeling of the output variable may remain unchanged. The purpose of RFTQM is to train the machine learning algorithm specifically on the patients which are considered low risk by the health care system. This may have the benefit of focusing the machine learning training step more clearly on the population the system is interested in. The drawback is that RFTQM has fewer positive examples to learn from. Generally, RFTQM tends to do well when the training population is large.

Claims Quantile Method

The Claims Quantile Method (CQM) is a version of the general method based on using claims data. Health care claims generally include records with information about the diagnosis (for example, in the ICD-9 or ICD-10 format), the costs incurred or allowed, and so on.

Proceed as described in the Risk Factor Quantile Method (RFQM) except that steps 1-4 can be replaced with the following:
1. Choose an EBS quantile level Q (for example, 80th percentile) and SRM quantile level M (for example, 10th percentile).
2. Collect a patient dataset of N patients.
3. For each patient, go through the claims and collect the amount allowed for the claim as well as all diagnosis codes (these are often in the form of ICD-9 or ICD-10 codes but some health care systems may use other formats). Demographic data such as age and gender can also be included if they are present.
4. For patient p and time period t, create the risk vector $R_{p,t}$ such that $R_{p,t}^i$ is the reading for the i-th piece of information specified in the previous step (i.e., claims code and/or cost).

Other steps are as discussed for the RFQM.

An advantage of the CQM is that it can incorporate claims data. Sometimes this may be the only data available. For example, the Centers for Medicare & Medicaid Services provides limited data set (LDS) files which have essentially only claims data plus very simple demographic information such as age and gender. These are large datasets which can be used to train or test machine learning algorithms.

As with the RFQM vs RFTQM, a Claims Trained Quantile Method (CTQM) can be defined by training the machine learning algorithm on the more focused set of examples defined in the RFTQM.

Disease Prediction Method

The disease prediction method is a version of the general method based on using predicted disease incidence. Some tools such as the BaseHealth Risk Engine can take patient data (for example, risk factors, vital signs, past claims data, or the like) and predict the likelihood of certain diseases (for example, heart disease, diabetes, or the like). These predicted disease risks can then be used to train an EBS using the Disease Prediction Method (DPM).

In the DPM, proceed as described in the Risk Factor Quantile Method (RFQM) except that steps 1-4 are replaced with the following:
1. Choose an EBS quantile level Q (for example, 80th percentile) and SRM quantile level M (for example, 10th percentile).
2. Collect a patient dataset of N patients.
3. For each patient, apply the desired disease prediction engine to obtain the risks for each disease.
4. For patient p and time period t, create the risk vector $R_{p,t}$ such that $R_{p,t}^i$ is the likelihood for that patient to develop disease i.

Other steps are as discussed for the RFQM. The advantages of the DPM may include:
1. The DPM can boil down a large amount of data about a patient into a more manageable set of disease risks.
2. Instead of having to learn everything from the given dataset, the DPM (when using the BaseHealth Risk Engine) can incorporate the existing scientific literature in mapping patient data to disease risks.

As with the RFQM vs RFTQM, a Disease Prediction Trained Method (DPTM) can be defined by training the machine learning algorithm on a more focused set of examples defined in the RFTQM.

Combined Quantile Method

The above-described methods can be used alone or either in parallel or combination. In the "combined method", the risk vector for method m (denoted $R_{p,t,m}$) could be determined and the combined risk vector could be formed by concatenating these together to form $R_{p,t}$.

For example, in the case where risk factor information such as blood pressure and cholesterol readings are available so that the RFQM could be applied and claims data is available so that the CQM could be applied, it may be valuable to combine the risk factor data and the claims data and use both. This may generally yield a better evidence-based score (EBS) than traditional simple risk measures (SRMs) such as the CMS HCC RAF score simply because the EBS may be built using more data than is available to the SRM.

Direct Methods

In the preceding methods quantiles were used. Quantiles have the following advantages:
1. Generally the system is interested in a list of patients for further analysis (for example, "the top 20%" or "the top 200"). In such cases the target list is inherently a quantile.
2. Simplifying the target to predict might improve training in machine learning algorithms. Hence trying to predict a simple binary label based on the quantile might be a more efficient goal than trying to predict the full future risk or cost of a patient.
3. Healthcare costs may increase as a result of inflation. In such circumstances, the estimated costs using previous years' data may not generalize well to the upcoming years. Using data quantiles can help to alleviate this problem.

Nonetheless, sometimes it is preferable to develop methods that directly estimate the target metric. The advantages of such direct methods include:
1. Some applications require a direct estimate of the target metric. For example, if the modeling goal is to estimate the healthcare costs of a population to allocate enough resources for their subsequent management, monetary costs may be the natural choice for the model output.
2. Having a direct estimate of the target metric could allow for flexibly determining the number of individuals to intervene with based on the difference between EBS and SRM.
3. In some cases, forcing the target measure to discrete categories may imply removing some useful information that could be otherwise used in the training step.

To address the above points, in this section the Risk Factor Direct Method (RFDM) is described. For the purpose of illustration, imagine that the simple risk measure (SRM) is the CMS HCC risk adjustment factor (RAF). To construct the evidence-based score (EBS) the following may be done:
1. Collect a patient dataset of N patients.
2. Choose R risk factors which affect health.
   Examples include patient age, systolic and diastolic blood pressure, lipid profile such as HDL, LDL, VLDL cholesterol measurements, triglycerides, and hemoglobin A1C and C reactive protein, body mass index.
3. For patient p and time period t, create the risk factor vector $R_{p,t}$ such that $R_{p,t}^i$ is the reading for the i-th risk factor for patient p in time period t.
   For example, the time could be the year or quarter such as "2015" or "Fall 2015".
4. For time period t+1, collect the target metric.
   A common target metric would be the total allowed claims in period t+1. Other target metrics are possible such as the RAF score in period t+1 or the number of hospital visits in period t+1.
5. Train a machine learning algorithm such as a linear regression, logistic regression, random forest, support vector machines, neural networks, or the like, to predict the target metric for patient p, as a function of the risk factor vector. This can be denoted as $L_p=f(R_{p,t})$ where $f(\bullet)$ represents the machine learning algorithm the system is training. For patient p, $f(R_{p,t})$ represents the evidence-based score. Note that in this case $L_p$ is not a binary label but a continuous value designed to predict the target metric (for example, the total claims cost).

Once the machine learning algorithm, $f(\bullet)$, is trained it can be used as follows for time period t':
1. Compute the discrepancy in EBS vs SRM for each patient.
   Two typical ways to measure discrepancy include subtraction and division (i.e., EBS-SRM or EBS/SRM).
2. Sort the patience by the EBS vs SRM discrepancy.
3. Select the top N patients, or the individuals for whom the discrepancy is above a certain threshold.
4. Pass this list to a team of health care professionals to triage and assess.

As described previously for quantile methods, variations of the direct method can be applied to obtain a list of methods including:
1. Risk Factor Direct Method (RFDM).
   This is as described above.
2. Claims Direct Method (QDM).
   As for the RFDM but using claims data instead of risk factor data similar to how the CQM is built as a variation of the RFQM.
3. Disease Prediction Direct Method (DPDM).
   As for the RFDM but using a disease prediction engine in a manner similar to how the DPM may be built as a variation of the RFQM.
4. Combined Direct Method (CDM).
   Combining the RFDM, QDM, and DPDM in a manner similar to how the CQM may be built as a combination of previous quantile methods.

Evaluation of Effect of Interventions

A common question faced by healthcare entities is to evaluate whether investing in a certain clinical or operational intervention program would result in an overall profit for them or not. As an example, a healthcare organization may want to know whether it overall results in positive return on investment (ROI) if it runs a campaign to reduce blood pressure in the population it controls, and if so, who exactly in the population should be the target to this intervention.

The risk models described earlier can be used to answer such questions. To this end, the models that include the risk factor of interest can be used as one of their inputs. Then the value of the risk factor to be intervened with can be updated to the values that are considered achievable after applying the intervention program. The updated values may then be submitted to the previously trained model to get new estimates for the target metric. The difference between the originally estimated target metric (when no intervention was in place) and the updated target metric (at the presence of the intervention) may provide an estimate on the effect of the intervention program.

As an example, consider an intervention program that reduces BMI of the participants on average by 20%. To evaluate the effect of such a program an EBS can be used. This EBS may be developed based on the clinical risk factors that may be relevant to the condition(s) of interest, and BMI may be among them. While any of the risk-factor-based methods described above, namely, RFQM, DPQM, RFDM, DPDM and their combinations, can be used in this context, the results from the direct methods, namely, RFDM and DPDM may be the most relevant because they directly evaluate changes in the target metric. To evaluate the effect of the proposed intervention program, for each individual in the population, the model may be run two (or more) times, once with the original BMI value and once with the updated BMI value after accounting for the effect of the intervention program. The difference between the target metrics in these two cases may determine the effect of intervention for the individual in question.

The fact that this analysis can be performed at an individual level may provide a fine-grained tool to analyze the effect of intervention programs at an individual level. The overall effect of the intervention program in the population can then be obtained by summing over the effects of the intervention program over the individuals that are finally selected to go under the intervention program.

Practical Tips

The following are two practical tips that could help in developing the machine learning models:
1. Sometimes due to the large levels of noise in the input variables, the correlation between them and the target metric may become erroneous, sometimes even opposite to what is expected by common science. One way to handle these cases when both the input and output variables take only positive values may be to use linear regression models and force the intercept in these models to zero. When both the input and output variables take only positive values, this could help to get a positive slope for the input variable.
2. When the target metric in the model is a healthcare cost, it might help to use the logarithm of the cost rather than the cost itself as the output variable. This transformation may help to control the subset of exceptionally costly individuals that typically exist in any population.

Model Extensions

There are a number of ways in which the methods described here can be extended. Several examples of such extensions are listed below:
1. The machine learning models may be developed so that they may use data in the time period t and predict the target metric in the time period t+1. However, in a variation the models can use data over any past time period, including t, t−1, t−2, or the like to predict the target metric at time period t+1. With this generalization, the risk vector may be a concatenation of the risk vectors obtained over any of the past time periods, namely, $R_{p,t}, R_{p,t-1}, R_{p,t-T}, \ldots, R_{p,t-T}$, where T+1 is the number of time periods used in the model.
2. The SRM can be described as a baseline measure with which the results of the EBS may be compared. The SRM, however, can also be used as an input variable to the machine learning models itself. In this way, the resulting model could exploit the predictive information in the SRM as well as other risk measures.
3. Accuracy of the proposed models may be expected to increase if they are developed in specific subpopulations. For example, it might help to develop different cost prediction models in populations with and without type 2 diabetes (a common chronic disease). Other examples may include developing models for smoker and non-smoker populations separately, or creating specific models for different age groups in a population. If a population is partitioned into a number of subpopulations, and a model is developed for each subpopulation, the results in the subpopulations can then be aggregated to get the overall result for the initial population.
4. Another way of increasing accuracy of the models is to try to break down the target metric into a number of sub-metrics and develop models for each sub metric separately. For example, suppose the goal is to predict the total claims due to ten common conditions (for example type 2 diabetes, coronary artery disease, breast cancer, or the like) Instead of developing a single model that predicts the total claims due to any of these conditions, one might get better results by developing different models, each with specific input variables, for each condition. Then the results of these models can be aggregated to get the total costs due to any of these conditions.

Concluding Remarks

The preceding discussion explains systems to optimally engage patients by using decision support tools and machine learning to find a cost effective health engagement plan. In general, some of the insights may include:
1. For various reasons, health care systems either implicitly or explicitly may use a simple risk measure (SRM) to determine which patients should receive proper health care.
2. The SRMs that may be used may often be developed based on limited data sources, may be outdated, may not be scientific or have other problems. As a result, existing methods of selecting patients for engagement or preventive care are often neither efficient nor cost effective.
3. By developing an evidence-based score (EBS) using modern decision support and machine learning tools along with a larger range of data, more accurate methods of identifying patients who could benefit from further engagement with the health care system and/or preventive care can be constructed.
4. By selecting patients with a relatively low SRM compared to the EBS, the system can identify patients that the current health care system is ignoring but who may be good candidates for engagement.

Since electronic health records (EHRs) are still evolving, the type and amount of patient data collected may differ significantly between different health care systems. Consequently, an improved manner to build the EBS may depend on both the SRM in use and the data available for a given health care system. To address this issue, a number of variations of the systems can be provided based on the type and amount of data available.

FIG. 1 illustrates a method according to certain embodiments. The method can include, at 110, obtaining a simple risk measure score for a patient. The simple risk measurement score can be calculated as described above.

The method can also include, at 120, obtaining an evidence-based score for the patient. The evidence-based score can be obtained in a variety of ways. For example, any of the following can be used: risk factor quantile method, risk factor trained-quantile method, claims quantile method, disease prediction method, combined quantile method, risk factor direct method, claims direct method, disease prediction direct method, or combined directed method. Each of these methods is discussed above. These and related methods, such as variations on the above-described methods, are also permitted.

The method can further include, at 130, comparing the simple risk measure score to the evidence-based score. This comparison may involve a first step of normalizing the scores to a common score system. For example, the score may represent a perceived risk of contracting a particular disease, expressed as a percentage or expressed in verbal terms (such as "not likely," "likely," "low risk," "high risk," or the like). Other scores may be expressed as a raw number from which a percentage or verbal description can be determined by, for example, looking up a translation table. Thus, for example, if the simple risk measure score is "healthy" and the evidence-based score is "60% chance of heart disease within 10 years," then the "healthy" value can be translated to "less than 10% chance of heart disease within 10 years," or the like.

The method can additionally include, at 140, identifying the patient as a target for preventative medicine based on a discrepancy revealed by the comparison. The identification can be further based on the simple risk measure score being below a threshold score. This use of a threshold may limit the identification to patients that are not likely to be treated based on their simple risk measure score.

The discrepancy can be the evidence-based score being a less healthy score than the simple risk measure score. This can be on an absolute basis, or this disparity or discrepancy being greater than a predetermined threshold. For example, the threshold could be a 50% discrepancy. For example, if the evidence-based score indicates a risk of 70% and the simple risk measure indicates a risk of 20%, then the patient could be identified as being suitable for preventative medicine.

The method can further include, at 150, administering or otherwise providing preventative medicine to the patient based on the identification.

Figure 2:
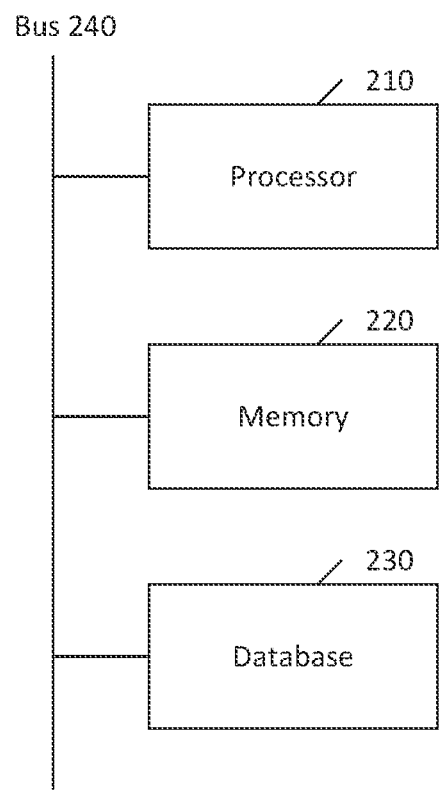
FIG. 2 illustrates a system according to certain embodiments.

The above method can be variously implemented, for example by computer system(s). FIG. 2 illustrates an example system that can implement the above-described methods in any of their variations.

As shown in FIG. 2, a system can include at least one processor 210 and at least one memory 220 including computer program instructions. The processor 210 and the memory 220 can be implemented separately or together. For example, the processor 210 and the memory 220 can be implemented on a same chip or on different computing systems.

The processor 210 can be any computational engine, such as any controller or central processing unit (CPU), having one processing core or multiple processing cores. The processor 210 may be a microprocessor, an application specific integrated circuit, or a field programmable gate array. Other implementations are also permitted.

The memory 220 can be any readable memory, such as a non-transitory computer-readable medium. The memory 220 can be any form of storage, such a optical storage, magnetic storage, or any form of random access memory (RAM) or read only memory (ROM).

The system can also include one or more database 230. The database 230 may be embodied in computer-readable medium, such as a storage array or hard disk drive. Other embodiments are also permitted.

The system can further include one or more bus 240, or other interconnection hardware. For example, the system can include one or more network interface cards, modems, or the like. The system is shown as though the bus 240 directly connects the processor 210, memory 220, and database 230, but other implementations are permitted. For example, the database 230 may be remote.

The at least one memory 220 and the computer program instructions can be configured to, with the at least one processor 210, cause the system at least to perform the above-described methods in any of their variations. The system can access database 230 to obtain various health-score-related data.

What is claimed is:

1. A method of identifying patients for assessment, performed by a processor executing software instructions stored in a memory, the method comprising:
    for each patient of a dataset of patients, calculating an evidence-based score (EBS), the calculating the EBS comprising:
        identifying one of more risk factors, and, for a time period t, calculate a risk factor vector $R_{p,t}$;
        for each patient, for a time period t+1, collecting a target metric;
        for each patient, determining whether the target metric in the time period t+1 is above a quantile level Q which is a percentile value;
        training a machine learning algorithm to predict a label $L_p$ for a patient p as a function of $R_{p,t}$, such that $L_p = f(R_{pt})$, where f( ) is the machine learning algorithm, and where $L_p$ is the EBS;
    identifying, from among a list of patients with a simple risk measurement below a quantile M, those patients with an EBS above a threshold value, for assessment;
    automatically generating a list of patients for assessment, the list containing those patients with a simple risk measurement below a quantile M and an EBS above the threshold value; and
    transmitting, to one or more healthcare professionals, the list of patients for assessment.

2. The method according to claim 1, wherein the identifying the one or more risk factors comprises identifying the one or more risk factors from a set comprising patient age, systolic and diastolic blood pressure, HDL cholesterol measurements, LDL cholesterol measurements, VLDL cholesterol measurements, triglycerides, hemoglobin A1C and C reactive protein, and body mass index.

3. The method according to claim 1, wherein the target metric is one of a total allowed claims data in the time period t+1, an RAF score in the time period t+1, and a number of hospital visits in the time period t+1.

* * * * *